US007234356B2

(12) United States Patent
Lia et al.

(10) Patent No.: US 7,234,356 B2
(45) Date of Patent: Jun. 26, 2007

(54) SHOCK RESISTANT BLOOD PRESSURE MEASURING APPARATUS

(75) Inventors: Raymond A. Lia, Auburn, NY (US); Robert L. Vivenzio, Auburn, NY (US); Raymond P. Dromms, Liverpool, NY (US); Bruce H. Schwager, Rochester, NY (US); Scott W. Osiecki, Skaneateles, NY (US); Robert S. Englert, Syracuse, NY (US); Chad P. Paris, Rochester, NY (US); Dale C. Saddlemire, Cortland, NY (US); Thomas J. Grant, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 38 days.

(21) Appl. No.: 11/081,331

(22) Filed: Mar. 16, 2005

(65) Prior Publication Data

US 2006/0207334 A1    Sep. 21, 2006

(51) Int. Cl.
*G01L 7/10*    (2006.01)
(52) U.S. Cl. .................................. 73/729.2
(58) Field of Classification Search ............. 73/729.2, 73/739, 756, 741
See application file for complete search history.

(56) References Cited

U.S. PATENT DOCUMENTS

| | | |
|---|---|---|
| 1,106,341 A | 8/1914 | Bristol |
| 1,328,876 A | 1/1920 | Hill |
| 1,377,032 A | 5/1921 | Starling et al. |
| 2,087,494 A | 7/1937 | Annin |
| 2,341,137 A | 2/1944 | Damron |
| 2,564,669 A | 8/1951 | Brady |
| 2,636,394 A | 4/1953 | Melchior |
| 3,797,315 A | 3/1974 | Halpern |
| 3,805,618 A | 4/1974 | Csaposs et al. |
| 3,874,242 A | 4/1975 | Csaposs et al. |
| 4,036,061 A | 7/1977 | Speidel |
| 4,040,298 A | 8/1977 | Lee et al. |
| 4,255,970 A | 3/1981 | VanPottelberg |
| 4,543,824 A | 10/1985 | Marterer |
| 4,552,153 A | 11/1985 | Newman et al. |
| 4,603,844 A * | 8/1986 | Chen ......................... 267/118 |
| 4,628,995 A * | 12/1986 | Young et al. ............... 166/113 |
| 4,685,336 A | 8/1987 | Lee |
| 5,181,422 A | 1/1993 | Leonard et al. |

(Continued)

FOREIGN PATENT DOCUMENTS

| | | |
|---|---|---|
| EP | 0 591 564 A1 | 10/1992 |
| EP | 0 705 563 A | 4/1996 |

(Continued)

*Primary Examiner*—Andre J. Allen
(74) *Attorney, Agent, or Firm*—Marjama & Bilinski LLP

(57) ABSTRACT

A pressure measuring apparatus includes a gage that is at least partially imbedded within a flexible elastomeric member disposed within an interior cavity of a device housing. A shock resistant member into which the gage is inserted permits fluid interconnection between the interior of the gage having a contained movement mechanism that is responsive to fluid pressure changes and a fluid source, such as an inflatable blood pressure cuff and further provides shock and/or impact resistance for a contained movement mechanism. Additional impact/shock absorption is provided by exterior features of the apparatus, including a peripheral bumper having a plurality of raised spring-like protrusions, and rubberized and contoured features of the device housing.

22 Claims, 9 Drawing Sheets

U.S. PATENT DOCUMENTS

| | | | |
|---|---|---|---|
| 5,320,169 A * | 6/1994 | Delatorre | 166/113 |
| 5,753,821 A | 5/1998 | Chou | |
| 5,966,829 A | 10/1999 | Lia et al. | |
| 6,036,718 A | 3/2000 | Ledford et al. | |
| 6,082,170 A | 7/2000 | Lia et al. | |
| 6,085,597 A * | 7/2000 | Miller et al. | 73/756 |
| 6,119,525 A * | 9/2000 | Hamma | 73/739 |
| 6,120,458 A | 9/2000 | Lia et al. | |
| 6,168,566 B1 | 1/2001 | Lia et al. | |
| 6,234,972 B1 | 5/2001 | Lia et al. | |
| 6,422,086 B1 | 7/2002 | Dromms et al. | |
| 6,481,291 B1 | 11/2002 | Lia et al. | |
| 6,578,428 B1 | 6/2003 | Dromms et al. | |
| 6,615,666 B1 * | 9/2003 | Lia et al. | 73/715 |
| 6,651,507 B1 * | 11/2003 | Hamma et al. | 73/741 |
| 6,679,122 B2 * | 1/2004 | Blake et al. | 73/739 |
| 6,783,500 B2 | 8/2004 | Dromms et al. | |
| 6,796,186 B2 | 9/2004 | Lia et al. | |

FOREIGN PATENT DOCUMENTS

| | | |
|---|---|---|
| FR | 2592297 A | 7/1987 |
| WO | 00/22983 A | 4/2000 |
| WO | 00/40941 | 7/2000 |

* cited by examiner

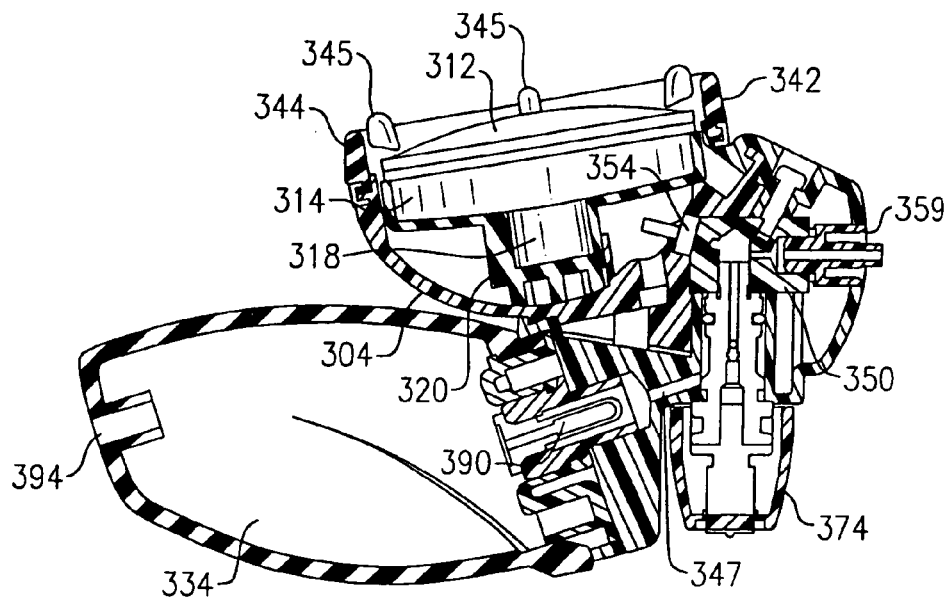
FIG.9
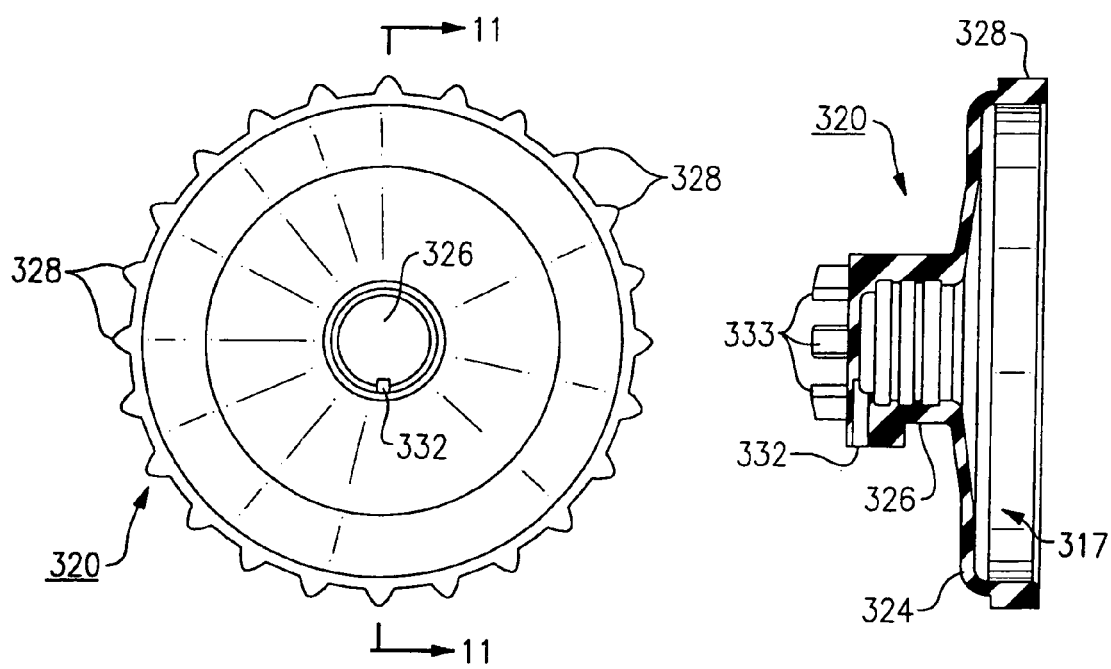
FIG.10
FIG.11

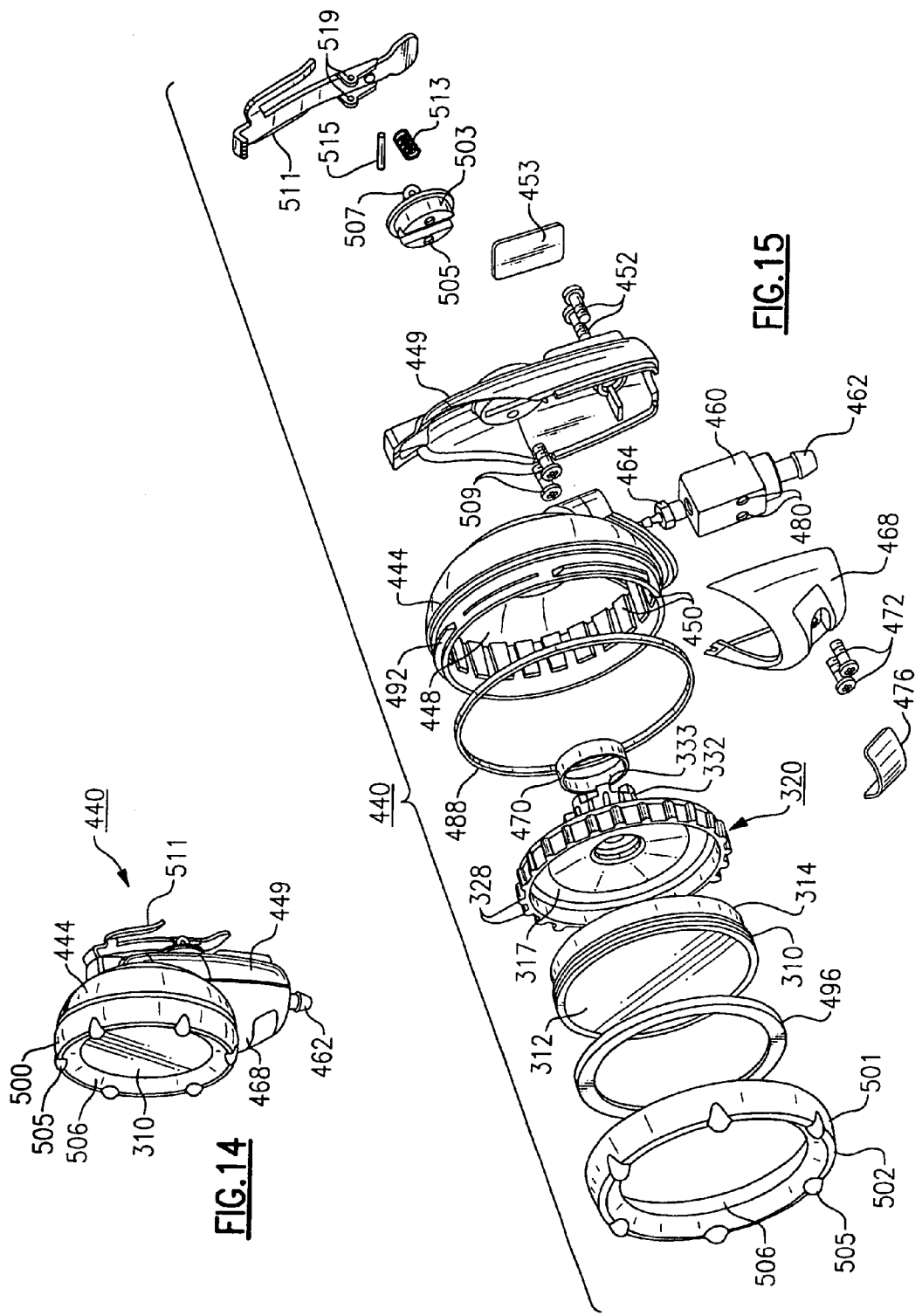

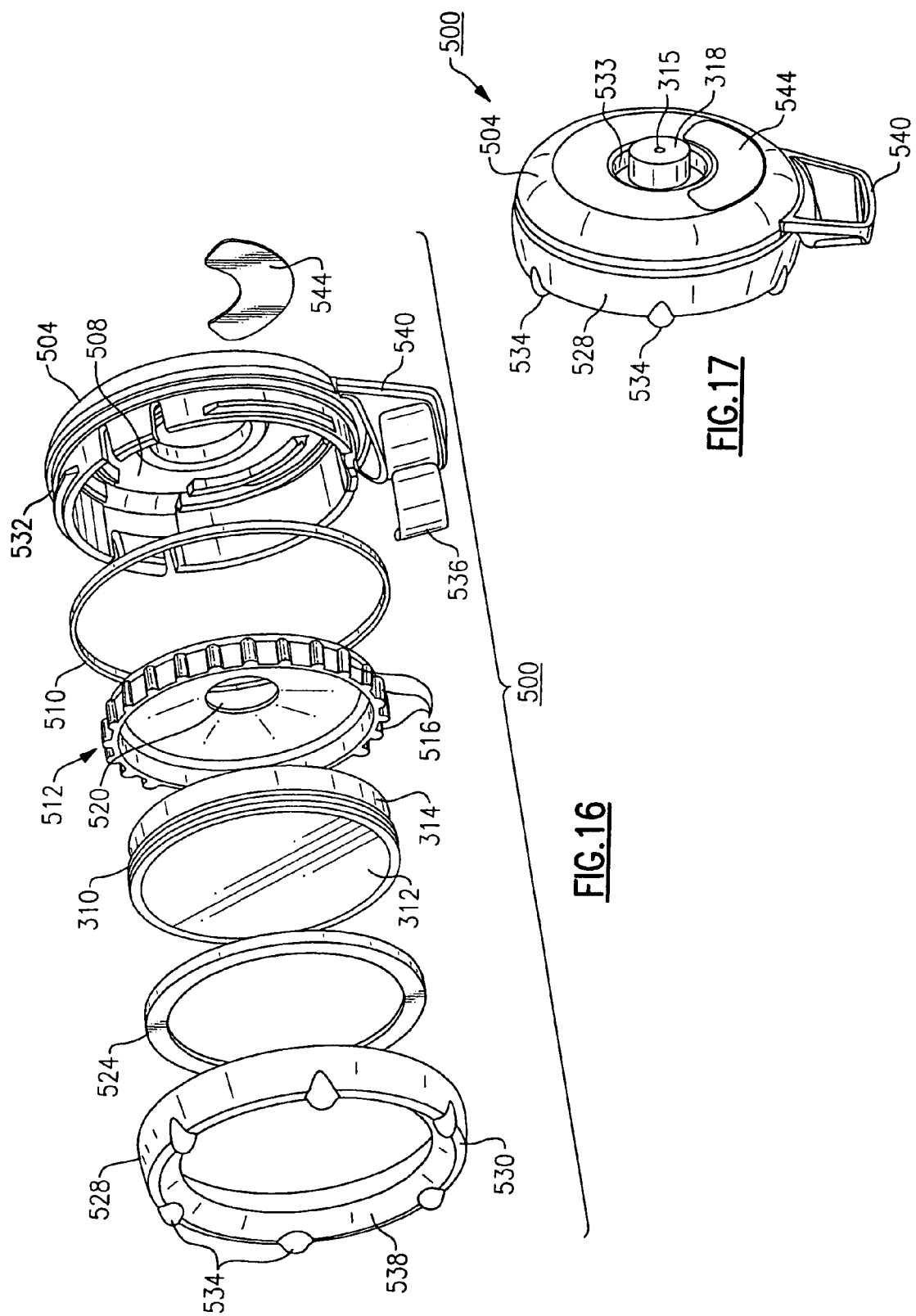

SHOCK RESISTANT BLOOD PRESSURE MEASURING APPARATUS

FIELD OF THE INVENTION

The invention relates to the field of pressure measuring apparatus and more particularly to an improved shock and/or impact resistant blood pressure measuring apparatus.

BACKGROUND OF THE INVENTION

Sphygmomanometers are commonly known in the field of medical diagnostic medicine as devices that are used by a clinician, a caregiver or a patient in order to measure the arterial blood pressure (ABP) of the patient. In brief, these pressure measuring devices commonly include a flexible inflatable sleeve or cuff that is wrapped around the limb of a patient, such as the arm or leg, and are attached to inflation means, such as for example, a pneumatic bulb or pump. A gage mechanism that is attached to the apparatus detects fluid pressure changes within the sleeve interior that provide diastolic and systolic pressure readings when used in combination with a stethoscope.

Recently, Applicants' have devised an improved gage mechanism that is useful for such devices, as well as other pressure measuring apparatus. This mechanism, as described in U.S. Pat. No. 5,966,829, the entire contents of which are herein incorporated by reference, utilizes a thin helically wound ribbon spring member that is secured at one end to an axial shaft member and to a fixed support of the apparatus of the remaining end. The shaft member is translatable and retains a measurement indicator and a dial face with indicia at one end while the remaining end of the translatable shaft member is placed into a position that can receive the output of a diaphragm or other pressure responsive element. As the sleeve inflates and deflates, the diaphragm moves and the shaft member is subsequently caused to move in an axial direction. Due to the constraint of the helically wound ribbon spring, however, the shaft member is also caused to rotate about its axis and circumferential movement is therefore also imparted to the indicating member relative to the dial face and its indicia. The above gage mechanism is elegant in its manufacture and relatively simple in design yet produces highly repeatable and accurate results with literally any parameter output in addition to pressure. Moreover, the mechanism is very compact as compared to typical gage movement mechanisms used for these purpose that are akin in their complexity to Swiss watches, requiring many more parts with higher tolerances, increased weight and a larger profile/envelope in order to retain the mechanism.

In later versions of the above gage mechanism, it was determined that the above axial design, due to its simplicity and ease of manufacture, could be placed in a housing that could be directly attached to the inflatable sleeve and moreover could be fluidly interconnected to the interior of the sleeve without the need of hoses or tubing. This concept is described in greater detail in U.S. Pat. No. 6,615,666, the entire contents of which are also incorporated by reference.

It is a general desire in the medical instrument field to be able to improve the shock bearing characteristics of blood pressure measuring apparatus, particularly the above-noted gage mechanism. Invariably, these apparatus are prone to drops from tables or other surfaces and/or other shock or impact type loads may be imparted thereupon that can prematurely disable or destroy their effectiveness. Recent attempts, as described in the afore incorporated U.S. Pat. No. 6,615,666, have further included the provision of a releasably or integrally mounted peripheral bumper that is placed in overlaying relation onto a portion of an upper portion of the gage housing, as well as the addition of a circumferential channel to the engagement end of the gage housing that mates with a socket of the inflatable sleeve. While these attempts have improved the overall durability of the blood pressure measuring apparatus, including the contained gage mechanism, from certain localized types of impact or shock loads, there is a continuing need to further improve the ability of these pressure measuring apparatus to generally withstand these types of loads.

SUMMARY OF THE INVENTION

It is therefore a primary object of the present invention to improve upon the above-noted prior art pressure measuring mechanisms.

It is therefore a further primary object of the present invention to provide a pressure measuring apparatus that is more durable and resistant to shock and/or impact loads than previous known apparatus, but whose design does not either sacrifice or diminish the overall performance characteristics or reliability thereof.

Therefore and according to a preferred aspect of the present invention, there is provided an apparatus for measuring blood pressure of a patient, said apparatus comprising:
  a device housing including an interior cavity and a pneumatic portion that is fluidly interconnected with said interior cavity;
  a gage housing, said gage housing including an upper cylindrical portion having a first diameter and a lower cylindrical portion having a second diameter which is substantially smaller than the first diameter, said upper cylindrical portion including a top window and said lower cylindrical portion including an opening extending into the interior of said gage housing, said gage housing further including a movement mechanism retained within the interior, said movement mechanism including means for detecting fluid changes in said interior cavity; and
  shock absorbing means for protecting the gage housing from shock and impact loads to said device housing, said shock absorbing means including means for retaining said gage housing in said interior cavity such that loads imparted to said device housing are not directed to said contained gage housing.

According to one variation, the shock absorbing means includes a tight fitting elastomeric retainer that is sized and shaped to receive said gage housing therein, said elastomeric retainer being fitted into the interior cavity of said device housing such that shock and/or impact loads will be absorbed by facets of the elastomeric retainer and will not be imparted to the contained gage housing. Preferably, the elastomeric retainer includes a plurality of spaced ribs on the exterior thereof that are in contact with the interior walls of the device housing, the ribs being configured to receive any of the shock and impact loads, the elastomeric retainer further including an opening to permit fluid interconnection between said interior cavity and the interior of said gage housing.

According to another variation, the gage housing is mounted in relation to an elastomeric gasket that is suspended within the device housing. The elastomeric gasket similarly is designed in order to absorb shock and/or impact loads before these loads can be imparted to the gage housing while not interfering with the fluid interconnection between the interior of the gage housing and the pneumatic portion of the device. According to one version, the elastomeric gasket includes a disc-like member that includes a center port for receiving the engagement end of the gage housing, the center port being disposed in relation to an existing fluid port in the device housing to enable fluid interconnection.

Preferably and according to one preferred embodiment, the movement mechanism includes an axial shaft member that is translatable and is supported for movement wherein a thin ribbon spring member is wound onto the exterior of the shaft member. One end of the thin ribbon spring member is attached to a fixed support while the remaining end of the spring member is attached to the axial shaft member. The upper end of the axial shaft member is attached to an indicating member wherein movement of a diaphragm or other pressure responsive member causes translation of the axial shaft member. This axial movement is constrained due to the attachment of the thin ribbon spring member, thereby causing rotation of the shaft member in addition to the translation and further causing circumferential movement of the indicating member relative to indicia provided on a dial face that can be seen in the window of the upper retaining portion of the gage housing. Alternatively, however, the movement mechanism can assume other mechanical and/or electronic designs.

Advantageously, the ribs that are provided on the exterior of the tight-fitting elastomeric retainer and preferably on the sides and the bottom thereof as well, when situated within the interior cavity of the device housing, effectively permit the absorption of shock or impact loads such that these loads are not transmitted to the contained gage mechanism. In addition and to provide protection for the upper portion of the retained gage housing, an external peripheral bumper is also provided to prevent damage to the top window of the gage housing and to prevent or minimize shock or impact loads from being transmitted to the upper portion of the device housing.

The device housing is further shaped and configured to withstand various forms of loading, such as those caused in the routine handling of such an apparatus. For example, the device includes an upper peripheral bumper which protects the face of the gage from shock loads, the bumper including a set of spring-like exterior protrusions as well as a web flange each of which flex and/or absorb shock loads when the gage mass pushes forward during a drop toward the face side of the apparatus. Additionally, an external rigid ring is interposed between the upper peripheral bumper and the face surface of the gage. The device housing is further contoured and shaped in order to provide additional shock and impact resistance for the entire mass of the assembly.

The pneumatic portion can be provided directly within the device housing or can be provided separately wherein the device can be directly attached according to one variation to a socket provided on an inflatable sleeve.

An advantage of the present invention is that a pressure measuring device is provided that is far more tolerable of shock and impact loads than any previously known device in the field.

Another advantage of the present invention is that the inclusion of the herein described shock absorbing and impact resistant features of the present invention does not significantly impact either the cost or the manufacture of the apparatus, nor do these features degrade either the performance or efficiency thereof Another advantage realized by the present invention is that one common pressure measurement movement device can be effectively used for both hand-held and so-called "pocket-style" gages.

These and other objects, features and advantages will become readily apparent from the following Detailed Description which should be read in conjunction with the accompanying drawings.

BRIEF DESCRIPTION OF THE DRAWINGS

FIG. 9 is a side elevation view, partly in section, of the pressure measuring apparatus of FIGS. 7 and 8;

FIG. 10 is a top view of a elastomeric retainer that receives a gage housing and is used in the pressure measuring apparatus of FIGS. 7–9;

FIG. 11 is a side view, partly in section, of the elastomeric retainer of FIG. 10;

FIG. 14 is a perspective view of a pressure measuring apparatus made in accordance with a sixth embodiment of the present invention;

FIG. 15 is an exploded view of the apparatus of FIG. 14; and

FIG. 16 is an exploded view of a pressure measuring apparatus in accordance with a seventh embodiment of the present invention; and FIG. 17 is a rear perspective view of the pressure measuring apparatus of FIG. 16.

DETAILED DESCRIPTION

The following discussion relates to several embodiments of an integrated blood pressure measuring apparatus which is made in accordance with the present invention. It will be readily apparent from the discussion which follows, however, that other forms of pressure measuring equipment such as, but not limited to barometers, pressure gauges, indicators, and the like can also effectively utilize the concepts that are described herein. Additionally, it is believed that the output of any transducer in response to a parameter, such as temperature and force, can also similarly utilize the inventive concepts described herein. It should further be noted that throughout the course of discussion that follows, certain terms such as "top", "bottom", "above", "below", "over", "beneath" and the like are used. These terms, however, are provided merely in order to give a suitable frame of reference with regard to the accompanying drawings. Therefore, these terms should not be regarded as limiting except where specifically indicated.

Figure 1:
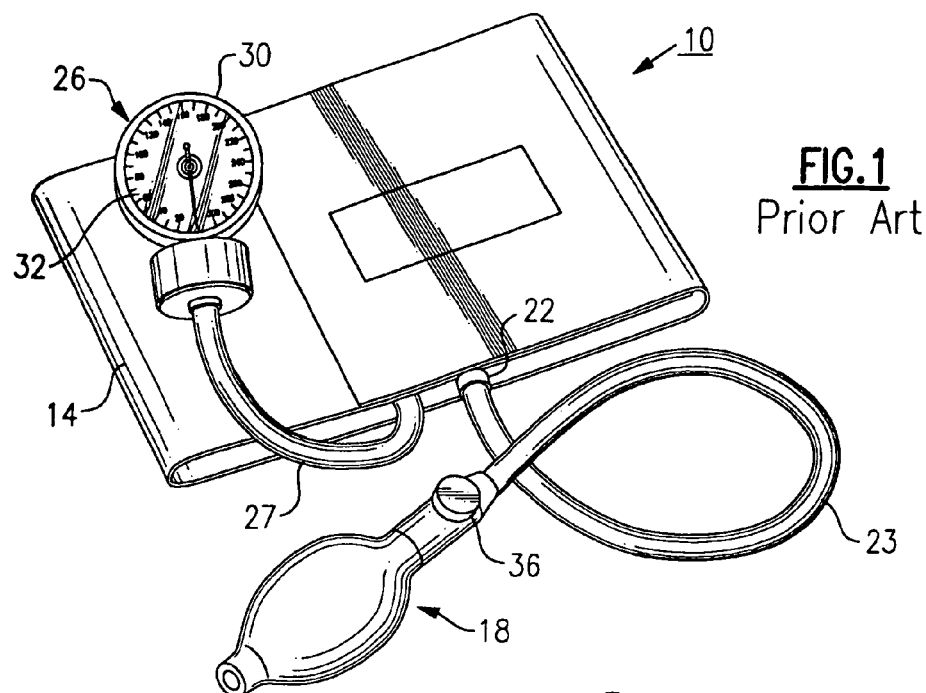
FIG. 1 is a top perspective view of a known pressure measuring apparatus.

Referring to FIG. 1, a typical blood pressure measuring instruments (i.e., sphygmomanometers), indicated herein as 10, includes an inflatable sleeve or cuff 14 that can be wrapped about a limb (e.g., an arm or leg (not shown)) of a patient. The sleeve 14 is inflated by means of a pneumatic assembly 18 which includes a hose 23 interconnected to a port 22 provided on the sleeve, thereby providing a fluid path to the interior of the sleeve 14.

A gage 26 is also separately tethered through a hose 27 to an adjacent port of the inflatable sleeve 14 and is in fluid communication with the interior of the sleeve, the housing including a dial face 30 which includes measuring indicia 32. A movement mechanism (not shown) provided within the interior of the gage 26 is responsive to changes in pressure of the sleeve interior and causes an attached indicating member to move relative to the measuring indicia 32 on the dial face 30 as the sleeve 14 is inflated and deflated using the pneumatic assembly 18. A stethoscope (not shown) is used to monitor the heartbeats of the brachial artery (when the sleeve 14 is wrapped onto a patient's arm) and to determine systolic and diastolic pressure of the patient, using the gage 26 as the sleeve is inflated to an appropriate inflation pressure and then deflated using a bleed valve 36.

Figure 2:
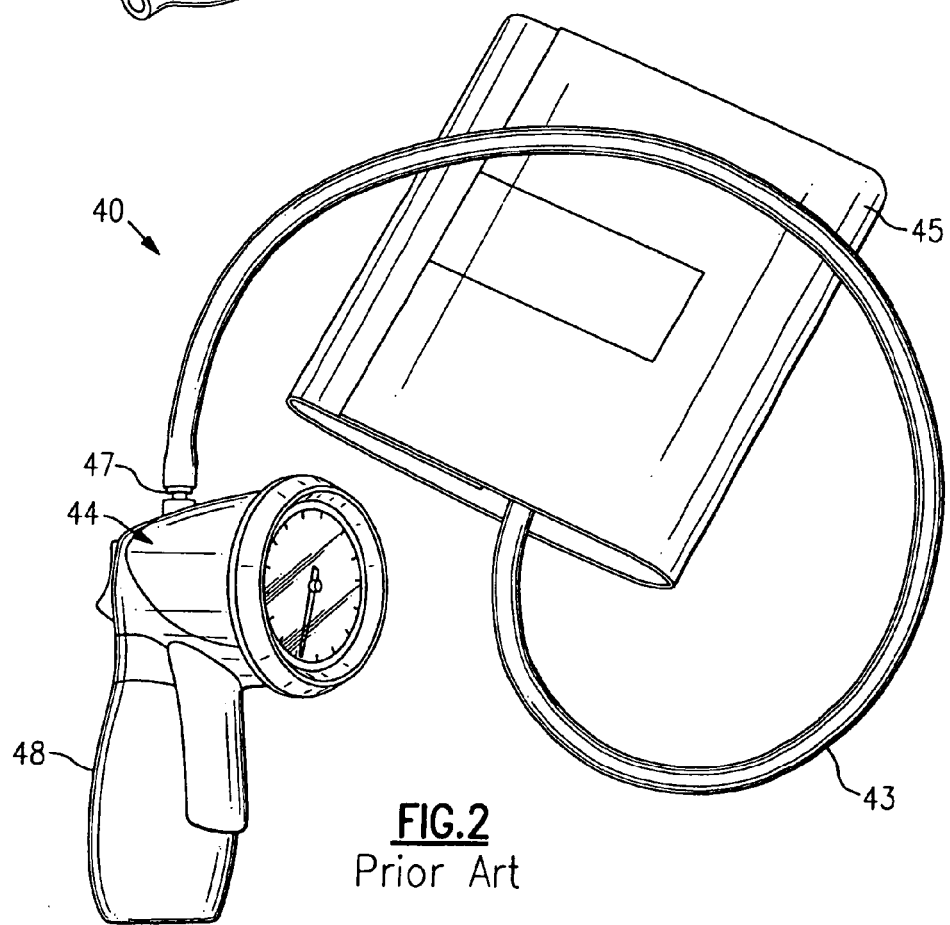
FIG. 2 is a top perspective view of another known pressure measuring apparatus.
Figure 3:
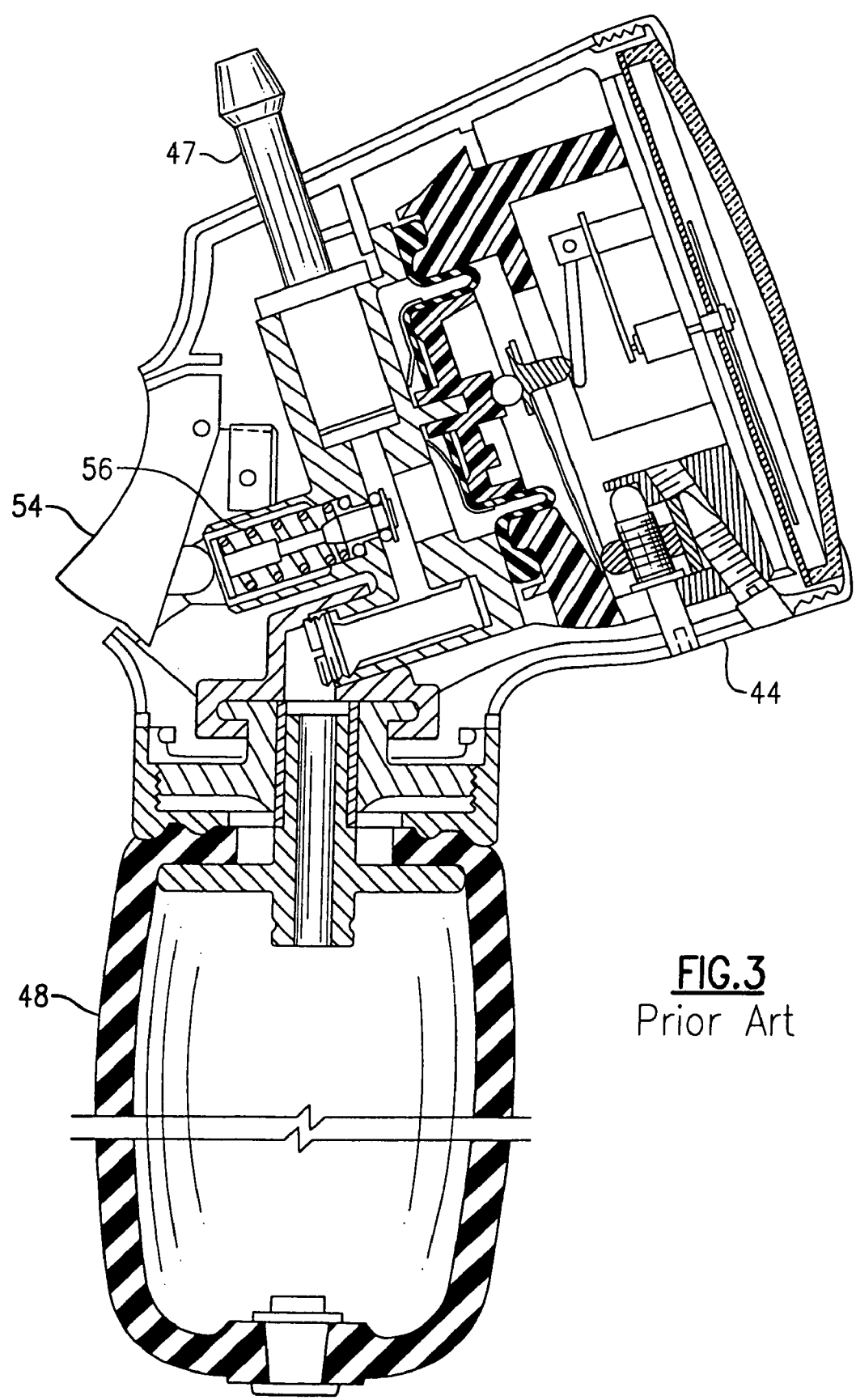
FIG. 3 is a front elevational view, shown in section, of a portion of the known pressure measuring apparatus of FIG. 2.

General efforts have been made to further incorporate features of sphygmomanometers together. One such apparatus 40, shown in FIGS. 2 and 3, incorporates a gage 44 having a pneumatic bulb 48 which is attached to the bottom of the gage 44 in a hand-held assembly. This integrated device 40 is also fluidly connected through a hose 43, one end of which is attached to a port 47 provided in the gage 44, to the interior of an inflatable sleeve 45 (shown only in FIG. 2) and includes a trigger 54, (shown only in FIG. 3) which enables valving 56 (also shown only in FIG. 3) to permit deflation of the inflatable sleeve. As previously noted, however, this particular device, is relatively complex and includes a significant number of intricate parts between the bulb 48 and the gage 44 for successful operation.

Figure 4:
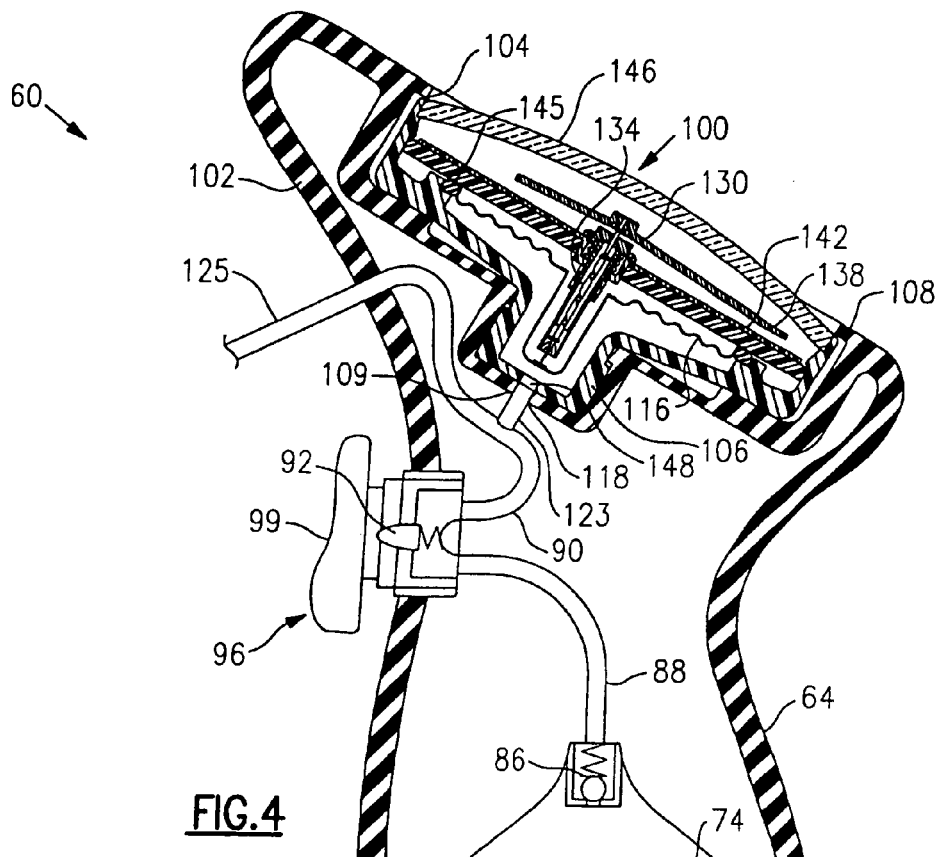
FIG. 4 is a partial side elevational view, shown in section, of a pressure measuring apparatus according to a first embodiment of the present invention.

With the preceding discussion serving as background and now referring to FIG. 4, there is shown an integrated blood pressure measuring apparatus 60 in accordance with the present invention including an elastomeric sleeve 64 which is sized and shaped to permit a lower portion 68 thereof to be hand-held. Preferably, the sleeve 64 is manufactured from a flexible moldable material, such as, for example, medical grade PVC, the sleeve further also being fluid impermeable. A flexible depressable bulb 72 is disposed within the lower portion 68 of the sleeve 64 that can be squeezed by the user. A lower portion 76 of the depressable bulb 72 includes a first one-way valve 80 disposed in relation to an inlet port 84 disposed at the bottom of the sleeve 64. A second one-way valve 86 attached to an upper portion 74 of the depressable bulb 72 prevents air from reentering the depressable bulb 72.

A hose 88 extends from the upper portion 74 of the depressable bulb 72 to a trigger assembly 96. The trigger assembly 96 according to this embodiment includes a bleed valve 92 that is connected to one end of the hose 88 extending from the depressable bulb 72, as well as hose 90. The bleed valve 92 is engaged by an actuable trigger 99 that is biasedly attached thereto, the trigger projecting from the exterior of the elastomeric sleeve 64.

A gage housing 100 is sealingly retained within an upper portion 102 of the elastomeric sleeve 64, preferably within an opening or pocket 108 which is smaller in diameter than the diameter of the gage housing so as to provide secure engagement therewith. The gage housing 100 according to this embodiment is defined by a substantially cylindrical shaped body that includes an upper portion 104 and a lower engagement end 106. The upper portion 104 has a first diameter which is substantially larger than the diameter (e.g., a second diameter) of the lower engagement portion. A movement mechanism contained within the gage 100 is responsive to pressure changes occurring within a fluidly interconnected inflatable sleeve (not shown) as described below.

Still referring to FIG. 4, the movement mechanism includes a diaphragm 116 which according to the present embodiment is horizontally arranged within the interior of the gage 100 having a movable surface. One end of a vertically arranged axial shaft member 130 is arranged in proximity to the movable surface of the diaphragm 116, the shaft member being supported for translatable movement. A thin helical ribbon spring 134, made from beryllium copper or similar flexible material, is wrapped about a portion of the shaft member 130. One end of the ribbon spring 134 is attached to a fixed supporting portion of the gage housing 100 while an opposite end of the spring is attached to an intermediate portion of the axial shaft member 130. An indicating member 138 is supported at the upper end of the shaft member 130 relative to a dial face 142 having suitable indicia (not shown) provided thereupon a top surface of the dial face. A transparent window 146 covers the upper portion 102 of the gage housing 100.

The lower engagement portion 106 of the gage housing 100 includes a port 148 that permits air/fluid to enter the interior of the gage housing for reasons described in greater detail below.

A lower portion of the retaining pocket 108 of the elastomeric sleeve 64 includes an opening 118 which is connected to one end of a hose section 123 extending therefrom. The diaphragm 116 is sealingly mounted within the interior by means of an O-ring 145, creating a fluid-tight seal within the gage housing 100.

The hose 90 extending from the trigger assembly 96 splits into two sections 123, 125 at a T-section. Hose section 123 extends to the port 148 formed in the gage housing 100 through an aligned opening 109 in the retaining pocket 108 while hose section 125 extends from the device 60 to an inflatable sleeve (not shown).

In operation, the lower portion 68 of the elastomeric sleeve 64 is squeezed, thereby causing air to be drawn into the pneumatic bulb 72 through the one-way valve 80 and out of the top of the bulb through hose 88. The bleed valve 92 of the trigger assembly 96 is initially closed and therefore air is directed both to the interior of the inflatable sleeve (not shown) and the gage housing 100 through hose sections 123, 125, respectively. Air entering the gage housing 100 through opening 109 and port 148 causes movement of the diaphragm 116, as well as corresponding axial movement of the shaft member 130. As the shaft member 130 translates upwardly, the flexion of the helical wound thin ribbon spring 134 against the fixed support of the gage 100 causes the shaft member to rotate and cause corresponding circumferential movement of the indicating member 138, relative to the indicia on the dial face 142. Additional details concerning the movement mechanism and the gage housing 100 are provided in U.S. Pat. No. 5,966,829, the entire contents of which were previously incorporated herein by reference.

Activation of the trigger 99 causes the bleed valve 92 to open, allowing deflation of the sleeve (not shown) and air to escape from the gage housing 100.

Figure 5:
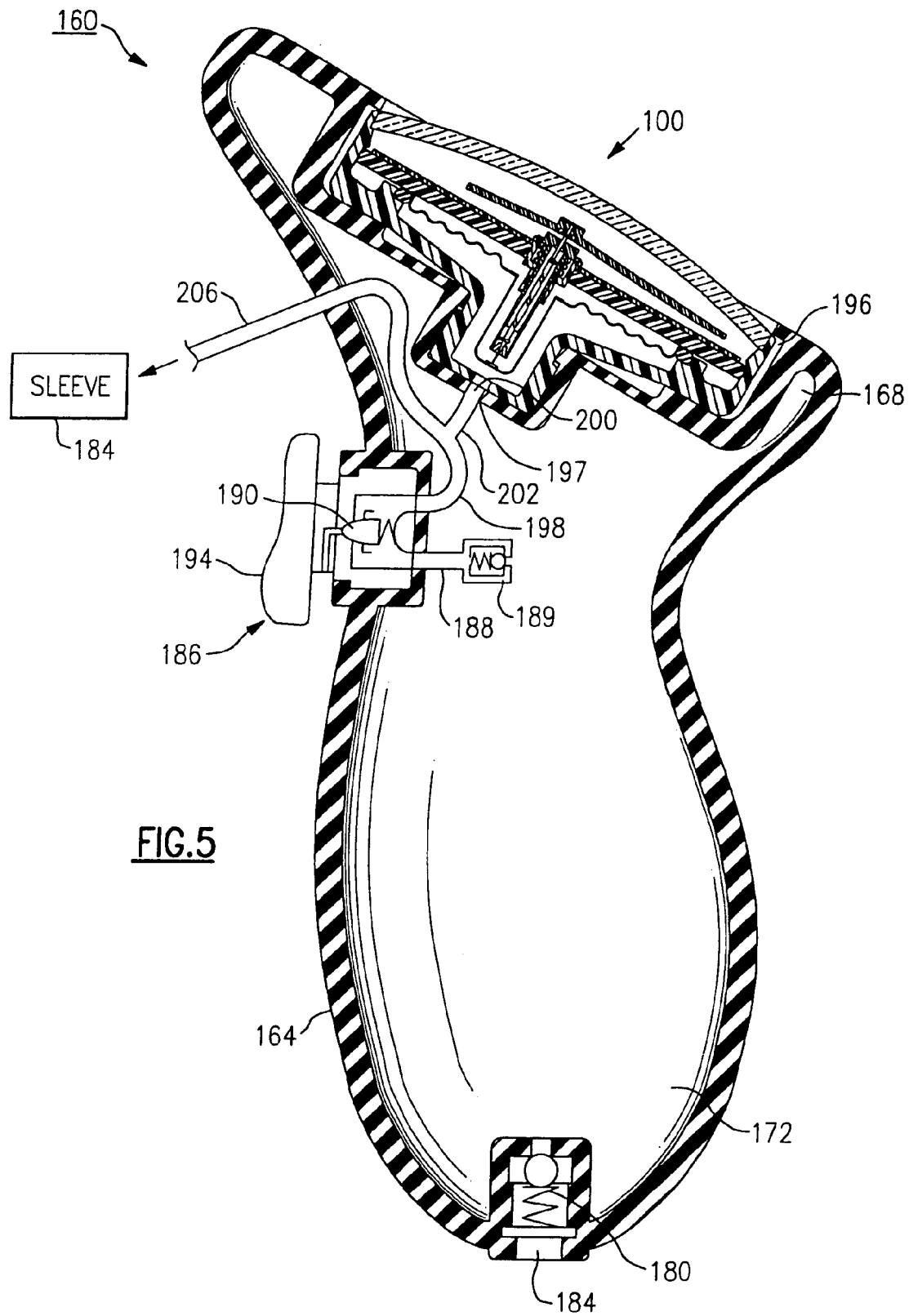
FIG. 5 is a partial side elevational view, shown partially in section, of a pressure measuring device according to a second embodiment of the present invention.

According to FIG. 5, a second version of an integrated blood pressure measuring apparatus 160 includes an elastomeric sleeve 164 similar in shape to the preceding and including an upper portion 168 and a contiguous lower engagement portion 172. According to this embodiment and in lieu of providing a pneumatic bulb within the lower portion 172 of the elastomeric sleeve 164, the sleeve itself provides the means for pneumatically inflating a blood pressure sleeve (shown diagrammatically as 184). A one way valve 180 provided at the bottom of the lower portion 172 of the sleeve 164 permits air to enter the interior of the sleeve when squeezed.

A trigger assembly 186 disposed along a wall of the sleeve 164 includes a bleed valve 190 which can be opened by means of an actuable trigger 194 provided on the exterior of the sleeve 164. The trigger 194 is biasedly connected to the bleed valve 190 through conventional means. A hose 188 extends into the trigger assembly 186, the hose including a valve 189 which permits air from the interior of the sleeve to pass into the hose 188. Another hose 198 extending from the trigger assembly 186, splits into sections 202, 206 respectively. Section 206 extends from the device 160 to the sleeve 184 and is connected to a port (not shown) which is in fluid communication with the interior of the sleeve.

The elastomeric sleeve 160 is similar to the sleeve 60 that was previously described above and includes a retaining pocket 196 which is preferably smaller in diameter than that of a fitted gage housing 100 to provide secure engagement with the exterior thereof. The gage housing of this embodiment 100 is also identical to that previously described above and includes a contained movement mechanism, such as described by previously incorporated U.S. Pat. No. 5,966,829, which permits circumferential movement of an indicating member relative to a dial face. Hose section 202 extends to a port 200 provided in the retaining pocket 196, thereby providing a fluid path through port 148, FIG. 4, and an aligned opening 197 into the interior of the gage 100.

In operation, lower portion 172 of the sleeve 164 is squeezed, permitting air to enter the interior of the sleeve and into hose 188 through check valve 189. Initially, the bleed valve 190 is closed. Therefore, air is directed through the trigger assembly 186 and through hose 198 and hose sections 202, 206 to the interior of the gage 100 and the sleeve 184, permitting inflation of the latter.

Air entering the interior of the gage 100 causes circumferential movement of the indicating member 138, FIG. 4, as previously described, based on the design of the movement mechanism, FIG. 4.

Opening of the bleed valve 190 is accomplished through use of the trigger 194 which permits deflation of the sleeve 184 whereupon a blood pressure measurement can be made.

Figure 6:
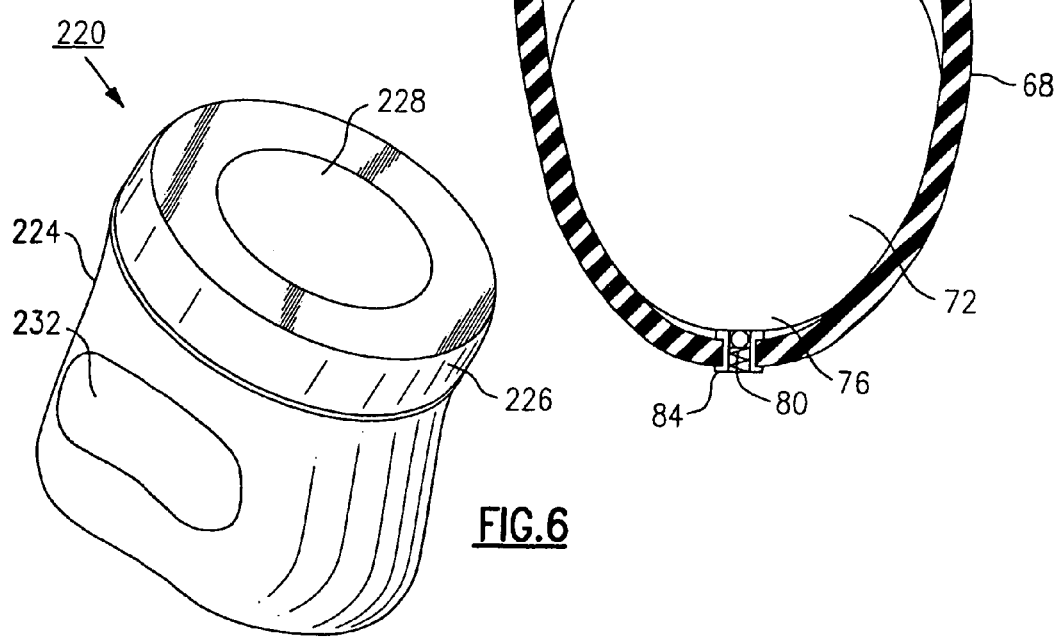
FIG. 6 is a perspective view of a pressure measuring apparatus in accordance with a third embodiment of the present invention.

Alternative designs incorporating the inventive concepts described herein are possible. For example, and referring to FIG. 6, a blood pressure measuring device 220 according to a third embodiment is shown. The device 220 is defined by a cylindrical sleeve 224 having an upper portion 226 which includes a retaining pocket 228 sized to sealingly engage a gage housing 100, FIG. 4, as previously described. The cylindrical sleeve 224 is elastomeric in nature and includes lower squeezable portions 232 to enable a pneumatic function. Alternatively, a pneumatic bulb (not shown) can be provided within the cylindrical sleeve 224 to permit inflation of a connected sleeve.

Figure 7:
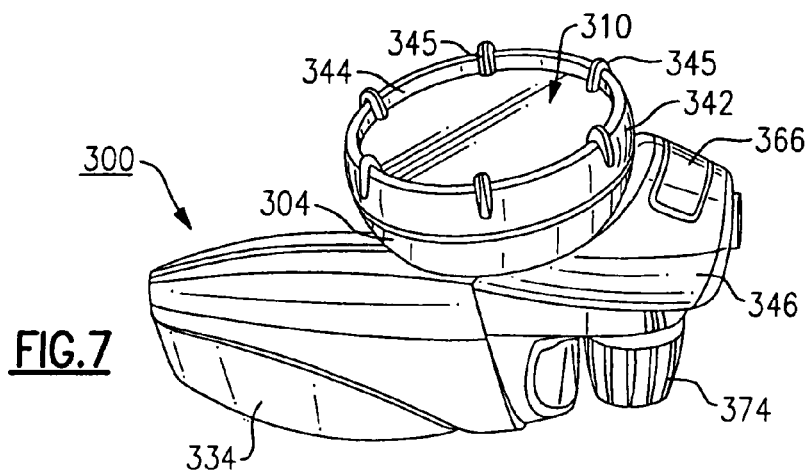
FIG. 7 is a side perspective view of a pressure measuring apparatus in accordance with a fourth embodiment of the present invention.
Figure 8:
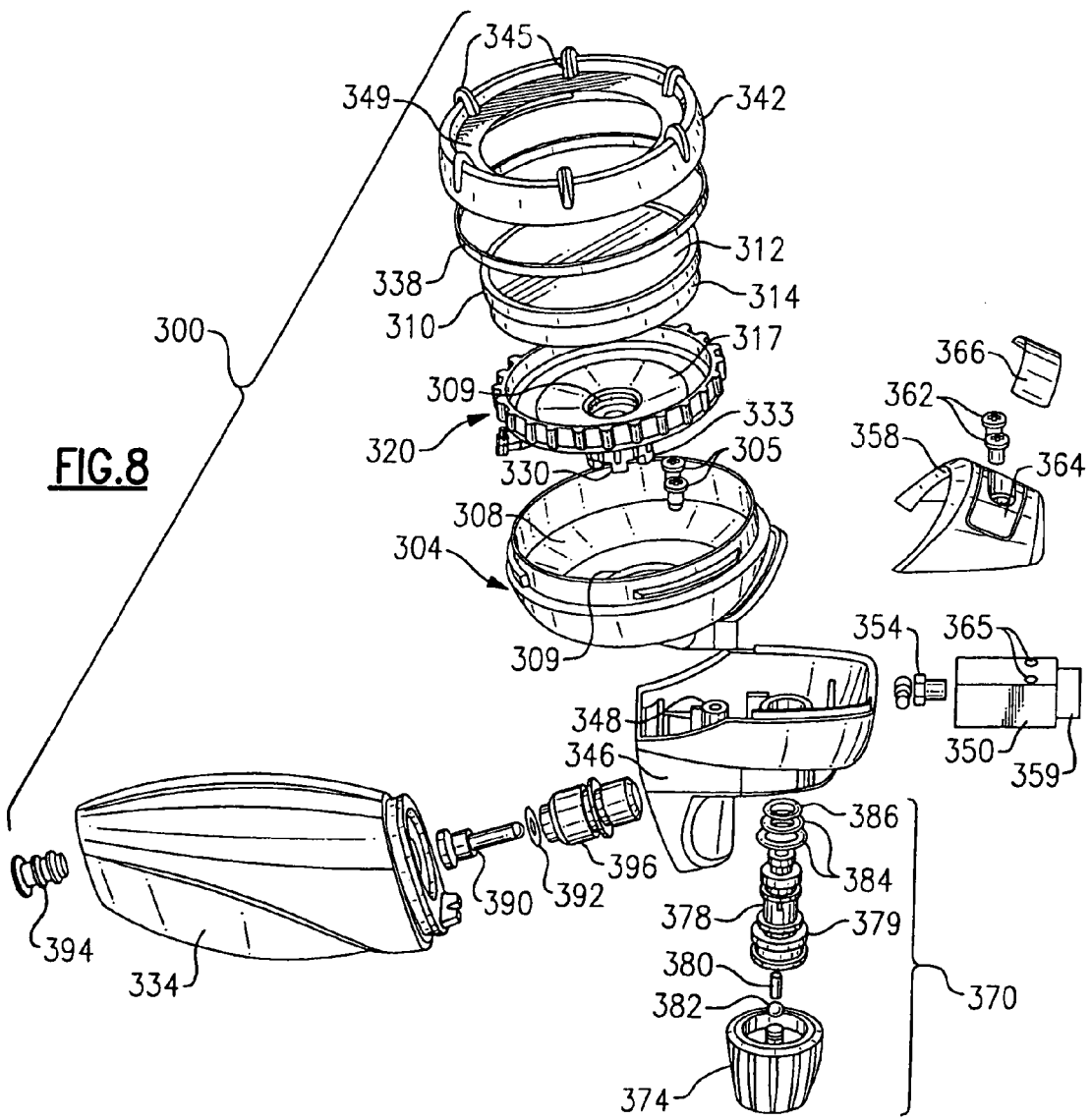
FIG. 8 is an exploded view of the apparatus of FIG. 7.

Referring to FIGS. 7–9, there is herein described yet another integrated blood pressure measuring apparatus 300 that is made in accordance with a fourth embodiment of the present invention. The measuring apparatus 300 according to this embodiment includes a cup 304, made preferably from a plastic molded material, that includes a defined interior cavity 308. The interior cavity 308 is sized to accommodate therein, a gage housing 310, such as described above and in previously incorporated U.S. Pat. No. 6,120,458, the bottom surface of the cup 304 including an opening 309 extending into an attached pocket housing 346. The gage housing 310 is a cylindrical member having a hollow interior that is defined by an upper retaining portion 314 and a lower engagement portion or end 318. A movement mechanism (not shown), such as described in previously incorporated U.S. Pat. No. 6,120,458 is contained within the hollow interior of the gage housing 310, the lower engagement end 318 having an opening 315, FIG. 17, at its bottom surface that permits fluid (air) to enter the housing. According to this embodiment, the movement mechanism is mechanical in nature and includes an axial cartridge extending vertically relative to the bottom opening. A translatable shaft member includes a helical spring member, made from beryllium copper or a similar material, that overlies the exterior of the shaft member and is secured at respective ends to the shaft member and a fixed support. A diaphragm is disposed beneath the shaft member adjacent to the bottom opening. An indicating member is attached to an upper end of the shaft member. As incoming fluid (air) enters the housing, the diaphragm moves causing movement of an engagement end of the shaft member. This movement of the shaft member produces flexion of the attached helical spring member due to its fixed constraint, causing rotation of the shaft member and the attached indicating member. The upper retaining portion 314 of the gage housing 310 includes a transparent top window 312 which permits the user to view the movement of the indicating member relative to a dial face having measurement indicia.

For purposes of the present invention, it should be noted that the herein described movement mechanism and gage housing are intended to be examples. It will become apparent that other forms of contained movement mechanisms, mechanical as well as electrical in nature, can be contained within the gage housing. For example, the gage housing could include an electronic display or an LED (not shown) in lieu of the indicating member.

The gage housing 310 is retained within the interior 317 of a separate open-ended elastomeric retainer 320 which is designed to be tightly fitted to the exterior of the gage housing. Referring to FIGS. 10 and 11, the open-ended elastomeric retainer 320 is sized to effectively retain the gage housing 310, the retainer including an upper retaining portion 324 that conforms to the exterior of the cylindrical upper retaining portion 314 of the gage housing 310 and a lower retaining portion 326 that conforms to the lower engagement end 318 of the gage housing. A first plurality of radially extending nubs or ribs 328 are disposed on the exterior of the upper retaining portion 324 while a corresponding second plurality of exterior ribs 330 extending along the sides and the bottom of the lower retaining portion 326 are used to cushion the contained gage housing 310 from shock and/or impact loads. Each of the pluralities of ribs 328, 330 are sized to engage with the interior walls of the cup 304 when the gage housing 310 is inserted into the interior cavity 308. The lower retaining portion 326 of the elastomeric retainer 320 further includes a lateral opening or port 332 which when attached to the gage housing permits fluid (e.g., air) to pass from a pneumatic portion of the apparatus into the interior of the gage housing 310 as described in greater detail below. The port provides an interface connection wherein a seal is formed upon attachment around the engagement portion of the gage housing for air to be provided as input into the port 332.

The elastomeric retainer 320 also preferably includes a set of bottom extending teeth 333 from a bottom surface, forming an engagement end of the lower retaining portion 326 of the elastomeric retainer 320. Each of the teeth 333 are preferably rounded to form or define a curved profile at the distal end thereof to aid in positioning the retainer 320 into an opening formed in the cup 304.

Referring to FIGS. 7–9, an annular gasket 338 is attached to an upper portion of the cup over the peripheral edge of the gage housing and into contact with the interior surface of a peripheral bumper 342 which covers the open top end of the cup 304. This gasket 338 retains the window on the gage during impact. The peripheral bumper 342 is made from a highly elastomeric material and includes a center opening to permit viewing of the top transparent window 312, as well as a raised circumferential portion 344 that protects the window, as well as the top portion of the apparatus 300, from shock and/or impact loads such as those caused by dropping of the apparatus. The raised circumferential portion 344 includes a set of equally spaced exterior protrusions 345, also made from an elastomeric material and distributed about the center opening, each of the protrusions acting as springs capable of absorbing the shock of the entire unit during a drop. The peripheral bumper 342 further includes a web flange 349 which, when the bumper is attached, lies against the face of the gage, the flange being designed to flex as the gage mass pushes forward during a drop of the apparatus into the face of the gage.

The cup 304 is attached by a pair of screws 305 to the pocket housing 346 through aligned openings that are provided in the interior cavity 308 (not shown) and a pair of mounting posts 348 (only one of which is shown in FIG. 8) formed in the pocket housing, respectively. The gage housing 310 is attached at its lower engagement end 318 to a recess 309 formed in the bottom surface of the interior cavity 308, the interior of the gage housing being fluidly interconnected with a pneumatic assembly. The pneumatic assembly of this apparatus 300 comprises a depressable bulb 334 that is fitted at an outlet end or side to the pocket housing 346. A first one-way valve assembly is attached to an outlet side of the depressable bulb 334, the valve assembly including a one-way valve 390 having one end that is mounted within the confines of a metal channel 396, the valve being sealingly connected by means of a gasket 392. A second one-way valve 394 is attached to the inlet end of the depressable bulb 334. As shown more clearly in FIG. 9, the first one-way valve assembly extends from the outlet side of the depressable bulb 334 into the confines of the lower end of the pocket housing 346 from the metal channel 396 through a vent 347 formed in the pocket housing.

A manifold block 350 is also added to the confines of the pocket housing 346 and more particularly an upper portion thereof, the manifold block including a pair of openings 365 that permits attachment by screws 362 through openings 364 provided in a shield plate 358. The screws 362 are covered by a label 366. The manifold block 350 includes a first barb connection 354 on one end contained within the pocket housing 346 and a second barb connection 359 on an opposing side extending outside the housing permitting attachment to a hose (not shown) allowing fluid interconnection between the confines of the pocket housing 346 and the interior of an inflatable sleeve or cuff (not shown). The first barb connection 354 provides a fluid conduit into the confines of the cup 304.

A bleed valve assembly 370 is also attached to the pocket housing 346 in relation to the manifold block 350, as well as the receiving vent 347 of the pneumatic portion of the apparatus. The bleed valve assembly according to this embodiment comprises a rotatable knob 374 and an interconnected spool 379 that is integrally attached to a bleed valve 378. The spool 379 is attached to an engagement portion of the knob 374, the assembly further including a ball 382 and a spring 380 disposed therebetween. The bleed valve 378 includes an engagement end that is added to an opening in the pocket housing 346, the valve being sealingly attached to the pocket housing 346 by means of a pair of O-rings 384 and a gasket 386, completing the assembly.

In operation, air enters the pocket housing 346 as the depressable bulb 334 is squeezed though the second one-way valve 394. Air is drawn into the bulb 334 through the second one-way valve 394, but is not permitted to exit the bulb through this valve. Air is thereby permitted to be passed into the pocket housing through the vent 347 and through the manifold block 350. Air is then directed via the manifold block 350 via the barb connection 354 to the confines of the bottom of the cup 304 wherein air enters the lateral port 332 of the elastomeric retainer 320 and the bottom opening 315, FIG. 17, of the engagement end 318 thereof. Air is also directed to the inflatable cuff (not shown) from the manifold block 350 to the inflatable sleeve/cuff (not shown) thrown a hose (not shown) attached to the barb connection 359.

As the cuff/sleeve deflates, air is pushed back into the pocket housing 346 from the sleeve (not shown) through the barb connection 359 and into the manifold block 350. Fluid pressure changes are also imparted to the attached gage housing 310 and the contained movement mechanism (not shown) based on the fluid connection provided between the manifold block 350 and the sealed confines of the cup 304. Air is also passed to the bleed valve assembly 370, which is opened by means of the knob 374 which is rotated to permit air to be vented from the apparatus 300.

The elastomeric retainer 320 provides a means for protecting the gage housing 310 and the contained movement mechanism (not shown) from shock and/or impact loads that can be imparted to the apparatus 300. The radially extending ribs 328, 330 as well as the teeth 333 of the tight-fitting elastomeric retainer 320 protect or isolate the contained gage housing 310 from peripheral loads while the elastomeric peripheral top bumper 342 protects or isolates the entire mass of the housing, including the window 312, via the raised circumferential portion 344, including the plurality of exterior protrusions 345 and the web flange 349 which aid when a face drop occurs. The gage is further isolated by means of the gasket 338. Additionally, the profile of the device and the rubberized coating of the bleed-valve assembly as well as the pneumatic portion of the apparatus provide additional shock and/or impact resistance for the entire mass thereof.

Figure 12:
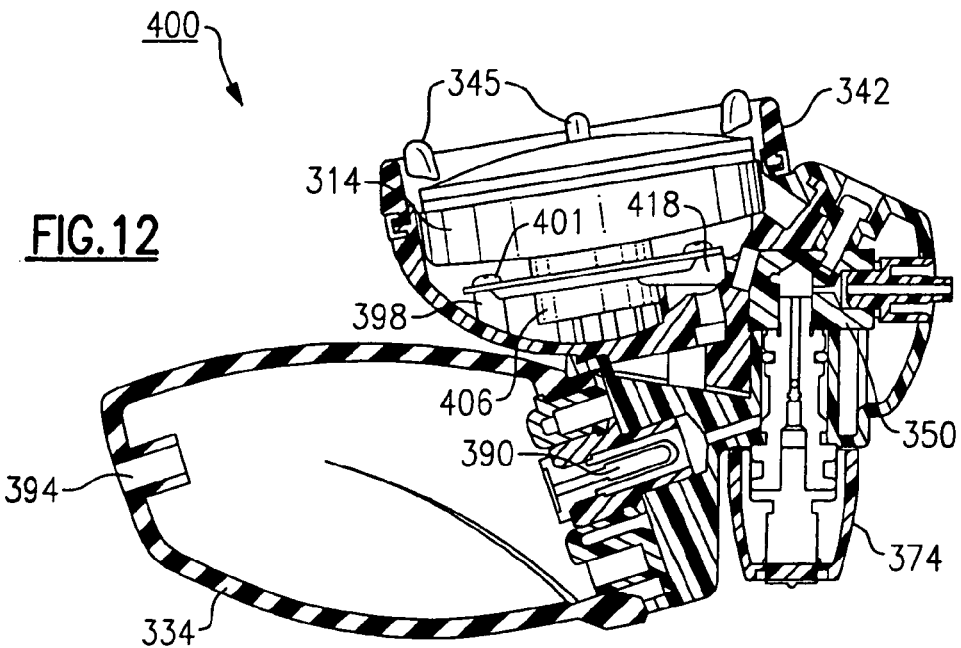
FIG. 12 is a side elevation view of a pressure measuring apparatus made in accordance with a fifth embodiment of the present invention.
Figure 13A:
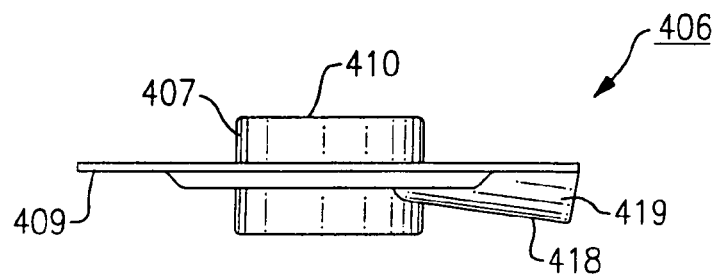
FIGS. 13(a) and 13(b) are side elevation and top perspective views, respectively, of an elastomeric gasket used in the pressure measuring apparatus of FIG. 12.
Figure 13B:
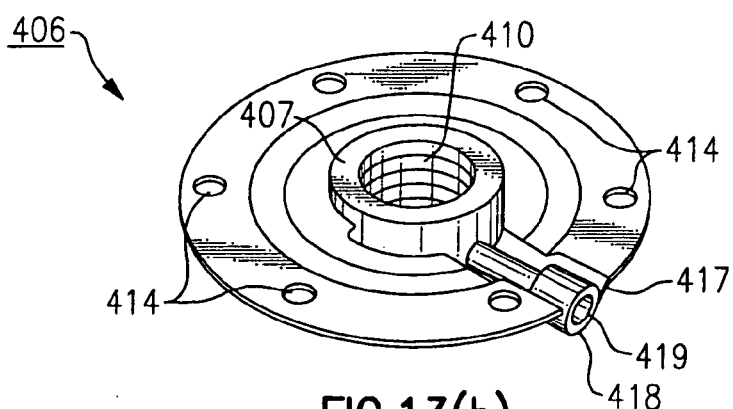

A fifth embodiment of a pressure measuring apparatus is disclosed in FIGS. 12, 13(a) and 13(b). The apparatus 400 is nearly identical to the apparatus 300 described in the preceding embodiment with respect to certain structural features including a gage housing 310, a cup 304 having an interior cavity 308 sized for retaining the gage housing 310, a pocket housing 346, a pneumatic assembly defined by a depressable bulb 334 and respective first and second one-way valves 390, 394, a bleed valve assembly 370, and a manifold block 350 contained within the pocket housing 346 that permits fluid interconnection between the pneumatic assembly, the confines of the pocket housing 346 and an inflatable sleeve/cuff (not shown). Therefore, for the sake of clarity, similar parts are herein labeled with the same reference numerals.

In lieu of a tight-fitting elastomeric retainer as described in the previous embodiment, however, the gage housing 310 is inserted into a highly flexible elastomeric gasket 406 which is mounted within the interior cavity 308 of the cup 304. The elastomeric gasket 406 is defined by a hollow open-ended tubular portion 407 having a top opening 410 disposed in a center portion thereof and a substantially ring-shaped peripheral portion 409 having an inner and an outer periphery extending radially from the tubular portion 407 at about the center of the axial portion thereof. The ring-shaped peripheral portion 409 includes a gap 417 which retains a lateral port 418 extending radially from the tubular portion 407, the port including a through opening 419 that extends to the hollow interior of the tubular portion 407. The tubular portion 407 of the gasket 406 and more particularly the diameter thereof is sized to accommodate the engagement end 318 of the gage housing 310. Disposed along the outer periphery of the elastomeric gasket 406 are a series of mounting holes 414 for permitting attachment to corresponding mounting posts 398 that are provided in the bottom surface of the cup 304.

In operation, a connected sleeve (not shown) is attached, using a barb connection to the manifold block 350 and inflated using the depressable bulb 334. The air transmitted to the manifold block 350 is also conduited to the confines of the cup 304 and through the opening 419 that is provided in the lateral port 418 of the elastomeric gasket 406. Air then enters the tubular portion of the gasket 406 and is directed into the bottom opening 315, FIG. 17, of the attached engagement end 318 of the gage housing 310, providing direct fluid interconnection with the remainder of the assembly wherein the attachment of the elastomeric gasket does not interfere with the measurement procedure. In the meantime, the application of shock loads to the cup 304 will result in the flexible gasket 406 absorbing the loads, the flexible gasket in effect acting to store energy similarly to that of a trampoline.

The remaining shock-absorbing aspects of the device are also found within the instant apparatus, however, including provision of an elastomeric gasket to cover the window of the gage housing and an upper peripheral bumper 342, as previously described, including a raised circumferential portion having a plurality of exterior spring-like protrusions as well as a flexible web flange.

There are other possible variations and modifications with regard to the integrated apparatus that can be imagined by those of sufficient skill in the field. For example and referring to FIGS. 14–15, a sixth embodiment according to the present invention is herein described. According to this embodiment, a tight-fitting elastomeric retainer 320, such as described above according to FIGS. 10 and 11, can be used to support a gage within an apparatus that is directly connected to an inflatable sleeve in lieu of the preceding pressure measuring apparatus having an integrated pneumatic bulb. As in the preceding, the same reference numerals are used to label similar parts for the sake of clarity.

In brief, the pressure measuring apparatus 440 according to this embodiment includes a substantially cup-shaped device housing 444 having an interior cavity 448, the housing being connected to a compact body portion 449 by means of a pair of screws 452 attached through respective openings that are formed in each of the housing and body portion, the openings being covered by a label 453. The interior wall of the cup-shaped housing 444 according to this embodiment includes a plurality of spaced inwardly directed tabs 450 arranged circumferentially. The open top of the cup-shaped housing 444 further includes a set of external threads 492.

A gage housing 310 is disposed within the confines of the interior cavity 448 of the device housing 444, the gage housing having fitted thereupon a tight-fitting elastomeric retainer 320 which is sized to engage the upper and lower engagement portions 314, 318 of the gage housing. The elastomeric retainer 320 includes a plurality of radially extending exterior ribs 328, 330 formed on tipper and lower retaining portions 324, 328 that are placed into contact with the interior wall of the cup-shaped housing 444, preferably the tabs 450, as well as a set of exterior teeth 333 that extend into contact with a recess (not shown) formed in the bottom wall of the cup-shaped device housing 444 along with an annular sealing ring 470 disposed therebetween.

A manifold block 460 includes a pair of extending barbs 464, 466 on opposing sides thereof that is fitted into a lower part of the compact body portion 449. The barb 464, when the manifold block 460 is disposed within the confines of the compact body portion 449, extends into a laterally extending exterior port 334 of the elastomeric retainer 320 to provide fluid interconnection with the interior of the received gage housing 310. The remaining barb 466 is used to attach to an inflatable sleeve or cuff (not shown).

The body portion 449 and contained manifold block 460 are covered by a shield plate 468 using a set of retaining screws 472 that are inserted through a pair of mounting holes and covered by a label 476, the screws being added to openings 480 in the manifold block 460, providing securement. As secured, the barb 462 extends therefrom.

An annular ring 488 is added to the exterior of the cup shaped housing 444 onto the external threads 492 and an elastomeric ring or gasket 496 is disposed between the interior of the elastomeric retainer 320 and the peripheral edge of the top window 312 of the gage housing 310. The latter, as previously noted, is used to retain the window on the gage during impact. A peripheral bumper 500 is secured to cover the above-noted components wherein the body portion 449 is attached to the cup shaped housing 444 by means of screws 452 which are attached through the bottom of the body portion and cup shaped housing, respectively. As previously noted, the peripheral bumper 502 includes a raised circumferential portion 502 having a center opening as well as a plurality of raised spring-like protrusions 505 and a flexible web flange 506 that lies against the face of the gage, the flange being designed to flex as the gage mass pushes toward a drop on the window.

A clip assembly is attached to the rear side of the compact body portion 449. The clip assembly according to this particular embodiment includes a circular mount member 503 having a pair of openings 505 that permits fixed attachment to the compact body portion 449 using fasteners 509. The rear side of the mount member 503 includes a lateral opening 507 permitting attachment of a spring clip member 511 by means of a spring 513 and a pivot rod 515 between a pair of spaced supports 519.

The operation of the pressure measuring apparatus 440 is now described briefly in which the extending barb 462 is used to attach a hose (not shown) to an inflatable sleeve which is separately attached to a pneumatic source, such as an bulb (not shown) or pump assembly (not shown). In this instance, fluid is directed from the hose into the manifold block 460 and into the confines of the gage housing 310 through the connection of barb 464 with the lateral port 332 of the elastomeric retainer 320. As such, fluid is then directed into the bottom opening 315, FIG. 17, of the engagement end 318 of the gage housing 310 and into the interior of the gage housing for use by the movement mechanism. The clip assembly permits the apparatus 440 to be attached either to the cuff/sleeve or alternatively to the user. In the meantime, the elastomeric retainer 320 provides interior isolation of shock and/or impact loads to the upper and lower portions of the gage housing 310 as well as the gasket 496 and the exterior features 328, 330, 333.

Outer protection is also provided with regard to the entire mass of the assembly. For example, any loads impartial to the top of the assembly 440 are absorbed by the elastomeric peripheral bumper 501 including the raised circumferential portion 502, raised protrusions 505 and web flange 506. Additional protection to other impacting sides of the apparatus are provided as well by the rubberized bleed valve knot and other componentry.

Yet another pressure measuring apparatus employing the present concepts and made according to a seventh embodiment is herein described with regard to FIGS. 16 and 17. As in the preceding, all similar parts are labeled herein with the same reference numerals for the sake of clarity.

According to this embodiment and unlike the preceding, the pressure measuring apparatus 500 includes a compact substantially cup-shaped housing 504 that can be directly engaged with a port integrally formed in an inflatable blood pressure sleeve (not shown). The port, as described in U.S. Pat. No. 6,615,666, includes a recessed engagement portion that includes an opening permitting fluid interconnection with the interior of the cuff.

The housing 504 further comprises an interior cavity 508 that is sized to retain a plurality of components including a gage housing 310 which is fitted into an elastomeric retainer 512. The gage housing 310 includes an upper retaining portion 314 and a lower engagement portion or end 318 that extends through a center opening provided in the elastomeric retainer 512. The retainer 512 further includes a plurality of equally spaced and radially extending ribs 516 that are circumferentially disposed along an outer periphery. As previously noted, the gage housing 310 includes a transparent window 312 which permits viewing relative movement of an indicating member against a dial face (not shown) having measuring indicia (not shown) disposed thereon. As previously noted, the movement mechanism used in connection with the gage housing 310 is an example of a mechanical version. It will be readily apparent that the shock-absorbing techniques herein described could further be employed for a retained electronic or other form of measurement apparatus that relies upon the input of fluid to determine pressure changes and also requires protection from shock and/or impact loads.

Still referring to FIGS. 16 and 17, an annular seal ring 524 is attached between the peripheral edge of the top window 312 of the gage housing 310 and a peripheral bumper 528 attached over a set of external threads 532 provided on a peripheral lip of the housing 504. This seal ring 524 provides shock protection as impact loads are imparted against the top window of the gage. An additional ring member 510 is attached onto external threads 532 provided at the top of the open end of the cup-shaped housing 504. An extending portion 540 of the housing 504 includes a label 536 attached thereto while a rear portion of the housing also includes a label 544.

In assembly, the gage housing 310 is first fitted within the interior of the elastomeric retainer 512 which fits in tight-fitting arrangement to the exterior wall of the upper retaining portion 314 of the gage housing. As noted, the lower engagement portion 318 of the gage housing 310 extends through the center opening 520 of the elastomeric retainer 512. The gage housing 310 and sleeve member 510, as assembled, can then be inserted into the interior cavity 508 of the cup shaped device housing, the housing having a similar center opening 533 aligned with the opening 520 and sized to accommodate the extending lower engagement end 318 of the gage housing 310. The ring member 510 is then attached to the exterior periphery of the circumferential lip of the device housing onto the external threads 532 wherein the peripheral bumper 528 is attached in overlaying fashion to complete the assembly after the seal ring 524 has first been introduced between the peripheral rim of the gage housing 310 and the interior surface of the peripheral bumper 528. The peripheral bumper 528 includes a raised circumferential portion 530 that includes a plurality of raised spring-like protrusions 534 as well as a flexible peripheral web flange 538 surrounding a center opening.

The extending lower engagement portion 318 of the attached gage housing 310 is sized for engagement within a pocket formed in the inflatable sleeve (not shown) as is described in greater detail in U.S. Pat. No. 6,615,666, the entire contents of which are incorporated by reference. The lower engagement portion 318 includes a center opening 315 that permits fluid interconnectivity with the interior of the inflatable sleeve (not shown) which is inflated by pneumatic means (not shown) including a bleed valve (not shown).

In the meantime, the elastomeric retainer 512 tightly surrounds the gage housing 310 and prevents shock and/or impact loads from being delivered to the gage housing and contained movement mechanism by means of the elastomeric material as well as the exterior rib features 516 provided on the outer periphery thereof that receive and dissipate loads imparted thereupon.

As in the preceding, the exterior features of the apparatus 500, including those of the peripheral bumper 528, the bleed valve knob, and the pneumatic bulb assembly provide shock resistance for the whole mass of the apparatus due to impact loading.

Additional alternative designs are possible. For example, it should be apparent that the elastomeric retainer can be formed with a lower portion sized to receive the lower engagement portion of the gage housing such that the lower portion can be extended into the pocket of the inflatable sleeve.

PARTS LIST FOR FIG. 1–17

10 blood pressure measuring instrument
14 inflatable sleeve or cuff
18 pneumatic assembly
22 port
23 hose
26 gage
27 hose
30 dial face
32 measuring indicia
36 bleed valve
40 apparatus 43 hose
44 gage
45 sleeve
47 port
48 pneumatic bulb
54 trigger
56 valving
60 integrated blood pressure measuring apparatus
64 elastomeric sleeve
68 lower portion
72 depressable bulb
76 lower portion—bulb
80 first one-way valve
84 inlet port
86 second one-way valve
88 hose
90 hose
92 bleed valve
96 trigger assembly
99 actuable trigger
100 gage housing
104 upper portion
106 lower engagement portion
108 pocket
109 aligned opening
116 diaphragm
123 section, hose
125 section, hose
130 axial shaft member
134 ribbon spring
138 indicating member
142 dial face
145 O-ring
146 transparent window
148 port
160 blood pressure measuring apparatus
164 elastomeric sleeve
168 upper portion
172 lower engagement portion
180 one way valve
184 sleeve
186 trigger assembly
188 hose
189 valve, check
190 bleed valve
194 actuable trigger
196 retaining pocket
197 aligned opening
198 hose
200 port
202 hose section
206 hose section
220 blood pressure measuring device
224 cylindrical sleeve
226 upper portion
228 retaining pocket
232 lower squeezable portions
300 integrated blood pressure measuring apparatus
304 cup
305 screws
308 interior cavity
309 recess
310 gage housing
312 transparent top window
314 upper retaining portion
315 opening, bottom
317 interior
318 lower engagement portion or end
320 elastomeric retainer
324 upper retaining portion
326 lower retaining portion
328 first plurality of ribs
330 second plurality of ribs
332 lateral opening
333 teeth
334 pneumatic bulb
338 trim ring
342 peripheral bumper
344 raised circumferential portion
345 exterior protrusions
346 pocket housing
347 vent
348 mounting posts
349 web flange
350 manifold block
354 barb connection
358 shield
359 barb connection
362 screws
364 openings
365 openings
366 label
370 bleed valve assembly
374 knob, rotatable
378 valve, bleed
379 spool
380 spring
382 ball
384 O-rings
386 gasket
390 one-way valve, first
392 gasket
394 one-way valve, second
396 metal channel
398 mounting posts
400 apparatus
406 elastomeric gasket
407 tubular portion
409 ring-shaped peripheral portion
410 top opening
414 mounting holes
417 gap
418 lateral port
419 port opening
440 apparatus
444 device housing
448 interior cavity
449 body portion
450 tabs
452 screws
453 label
459 retaining screws
461 holes
462 barb
464 extending barb
466 exterior port
467 label
468 shield plate
470 seal ring
472 retaining screws
476 label
480 openings
492 threads
496 seal ring 500 apparatus
502 raised circumferential portion
503 mount member
504 cup-shaped housing
505 raised protrusions
506 web flange
507 lateral opening
508 cavity, interior
509 fasteners
510 trim ring
511 spring clip member
512 elastomeric retainer
513 spring
515 pivot rod
516 ribs
519 spaced supports
520 center opening
524 seal ring
528 peripheral bumper
530 raised circumferential portion
532 external threads
533 opening
534 raised protrusions
536 label
538 web flange
540 extending portion
544 label While the present invention has been particularly shown and described with reference to the preferred mode as illustrated in the accompanying drawings, it will be understood by one skilled in the art that various changes in detail may be effected therein without departing from the spirit and scope of the invention as defined by the claims.

We claim:

1. A pressure measuring apparatus comprising:
   a gage housing containing a movement mechanism which is responsive to changes in fluid pressure, said gage housing having an engagement portion including at least one port for receiving a fluid;
   an apparatus housing having a defined interior cavity that is sized to retain said gage housing therein; and
   an elastomeric member surrounding at least a portion of the exterior of said gage housing that isolates impact loads imparted to said apparatus housing from said gage housing, while permitting fluid interconnection between the interior of said gage housing and a fluid source connected to said apparatus housing.

2. Apparatus as recited in claim 1, wherein said elastomeric member includes an elastomeric gasket, said elastomeric gasket including a center opening sized for receiving said engagement portion of said gage housing, said elastomeric gasket being fixedly attached to the interior of said apparatus housing and forming a force isolator between said apparatus housing and said gage housing.

3. Apparatus as recited in claim 2, wherein said elastomeric gasket further includes a fluid connection port connected to said fluid source.

4. Apparatus as recited in claim 1, wherein said elastomeric member includes a tight-fitting elastomeric retainer shaped to engage a portion of the exterior of said gage housing.

5. Apparatus as recited in claim 4, wherein said gage housing includes an upper retaining portion above said engagement portion, said upper retaining portion having a diameter which is larger than the diameter of said engagement portion, said elastomeric retainer being sized to at least the exterior of the upper retaining portion of said gage housing.

6. Apparatus as recited in claim 5, wherein said elastomeric retainer includes a center opening sized to permit the passage of said engagement portion.

7. Apparatus as recited in claim 5, wherein said elastomeric retainer is sized to accommodate the upper retaining portion and said engagement portion of the gage housing therein.

8. Apparatus as recited in claim 5, wherein said elastomeric retainer includes a plurality of spaced exterior ribs arranged to engage the interior wall of the device housing.

9. Apparatus as recited in claim 5, wherein said elastomeric retainer includes a fluid receiving port disposed in relation to the at least one port of said gage housing.

10. An apparatus as recited in claim 1, including a peripheral bumper attached to the top of said device housing, said peripheral bumper having a raised circumferential portion for covering a top window of said gage.

11. An apparatus as recited in claim 10, wherein the raised circumferential portion of said peripheral bumper is made from an elastomeric material and includes a plurality of raised protrusions configured for absorbing impact loads.

12. An apparatus as recited in claim 11, wherein said peripheral bumper includes a center opening for permitting a user to see a top window of said gage, said bumper including a flexible peripheral web flange disposed between said raised protrusions and said center opening.

13. An apparatus as recited in claim 12, including a peripheral ring member disposed between said top window of said gage and said peripheral top bumper.

14. A pressure measuring apparatus comprising:
   a gage having a housing;
   a device housing having an interior cavity into which said gage housing is disposed;
   a movement mechanism retained within said gage housing, which is responsive to changes in fluid pressure, wherein said gage further includes a port that permits fluid to enter the interior thereof; and
   elastomeric supporting means within said device housing for absorbing shock and or impact loads imparted to said device housing and into which at least an exterior portion of said gage housing is fitted, said elastomeric supporting means further including means for permitting fluid interconnection between a fluid source and the interior of said gage.

15. Apparatus as recited in claim 14, wherein said elastomeric supporting means includes an elastomeric retainer that is form fitted to at least a portion of the outer periphery of said gage for covering the exterior thereof, said elastomeric retainer further including at least one opening to permit fluid interconnection between the fluid source and the interior of said gage.

16. An apparatus as recited in claim 15, wherein said elastomeric retainer includes a plurality of exterior ribs for contacting the interior of said device housing.

17. An apparatus as recited in claim 16, wherein the plurality of exterior ribs are provided on the bottom and the side of said elastomeric retainer.

18. An apparatus as recited in claim 16, wherein at least one exterior rib is provided on the bottom of said retainer and contoured to follow a curved profile.

19. An apparatus as recited in claim 14, wherein said device housing is directly attachable to an inflatable sleeve.

20. An apparatus as recited in claim 14, wherein said apparatus is used to measure blood pressure.

21. An apparatus as recited in claim 14, wherein said elastomeric supporting means includes a flexible gasket having a center opening into which an engagement portion of said gage is disposed, said flexible gasket being fixedly mounted to the interior of said device housing within said cavity to form a force absorbing member.

22. An apparatus as recited in claim 21, wherein said flexible gasket includes a port to permit fluid interconnection of said gage with said fluid source.

* * * * *